(12) United States Patent
Huici

(10) Patent No.: US 11,938,276 B2
(45) Date of Patent: Mar. 26, 2024

(54) INDWELLING DOUBLE OR TRIPLE LUMEN URINARY CATHETER

(71) Applicant: HBIP Limited Liability Company, Casper, WY (US)

(72) Inventor: Bruce T Huici, Miami, FL (US)

(73) Assignee: HBIP LIMITED LIABILITY COMPANY, Casper, WY (US)

( * ) Notice: Subject to any disclaimer, the term of this patent is extended or adjusted under 35 U.S.C. 154(b) by 88 days.

(21) Appl. No.: 16/948,138

(22) Filed: Sep. 4, 2020

(65) Prior Publication Data

US 2021/0060291 A1 Mar. 4, 2021

Related U.S. Application Data

(60) Provisional application No. 62/895,538, filed on Sep. 4, 2019.

(51) Int. Cl.
*A61M 25/00* (2006.01)
*A61L 29/04* (2006.01)
(Continued)

(52) U.S. Cl.
CPC ....... *A61M 25/0017* (2013.01); *A61L 29/042* (2013.01); *A61M 1/77* (2021.05);
(Continued)

(58) Field of Classification Search
CPC ............ A61M 25/0017; A61M 1/0058; A61M 25/0026; A61M 25/10186; A61M 2205/02; A61M 2205/3368; A61M 25/0068; A61M 25/10; A61M 27/00; A61M 25/04; A61M 27/006; A61M 27/002; A61M 5/14276; A61M 2205/3331; A61M 2205/3334; A61M 2025/1052; A61M 39/22; A61M 2202/0464; A61M 39/24; A61M 25/0075; A61M 2039/248; A61M 1/77; A61M 2202/0496; A61M 25/1011; A61M 1/782;
(Continued)

(56) References Cited

U.S. PATENT DOCUMENTS 3,625,793 A * 12/1971 Sheridan ........... A61M 16/0434
156/244.18
3,884,242 A * 5/1975 Bazell ................. A61M 25/008
128/207.14
(Continued)

FOREIGN PATENT DOCUMENTS

GB  2465334 A1  5/2010
JP  H0984768  *  3/1997
WO  WO-2017074731 A1 *  5/2017  ........... A61B 10/007

OTHER PUBLICATIONS

PCT/US2020/070497 International Search Report dated Nov. 20, 2020.

*Primary Examiner* — Nicholas J. Weiss
*Assistant Examiner* — Brandon W. Levy
(74) *Attorney, Agent, or Firm* — Vance Intellectual Property, PC

(57) ABSTRACT

Herein is described a double or triple lumen, indwelling, urinary catheter having a bladder-protecting tip that has a drainage port centered at the end of the tips and a fitted check-valve. The catheter is useful for catheterizing patients whose bladders are in need thereof (e.g., due to a surgical procedure or other medical problem).

24 Claims, 9 Drawing Sheets

(51) Int. Cl.
  *A61M 1/00*  (2006.01)
  *A61M 25/10*  (2013.01)

(52) U.S. Cl.
  CPC .. *A61M 25/0026* (2013.01); *A61M 25/10186* (2013.11); *A61M 2205/02* (2013.01); *A61M 2205/3368* (2013.01)

(58) Field of Classification Search
  CPC ...... A61M 2039/062; A61M 25/10185; A61M 2210/1085; A61M 2210/1089; A61M 25/0082; A61M 2025/0081; A61L 29/042; F16K 15/04; F16K 27/0209; Y10T 137/791; Y10T 137/4501; Y10T 137/7873; Y10T 137/0508; A61F 5/4405; A61F 2/958; A61F 2/2433; A61B 17/12136; A61B 1/00082; A61B 10/007
  See application file for complete search history.

(56) References Cited

U.S. PATENT DOCUMENTS

| | | |
|---|---|---|
| 4,106,675 A | 8/1978 | Taylor |
| 5,250,029 A * | 10/1993 | Lin .................... A61M 25/1011 606/192 |
| 5,794,656 A * | 8/1998 | Breslin .................. F16K 15/04 137/533.11 |
| 5,800,339 A | 9/1998 | Salama |
| 10,179,232 B2 | 1/2019 | Huici |
| 2001/0047165 A1* | 11/2001 | Makower ......... A61B 17/12045 604/528 |
| 2003/0029508 A1* | 2/2003 | Raboin .................... F16K 1/307 137/614.05 |
| 2004/0172009 A1 | 9/2004 | Marisi |
| 2006/0165606 A1* | 7/2006 | Tarara ..................... A61P 11/06 424/46 |
| 2007/0161949 A1* | 7/2007 | Knox ................ A61M 25/0017 604/93.01 |
| 2008/0051763 A1 | 2/2008 | Frojd |
| 2011/0218520 A1* | 9/2011 | Andrich ................ A61M 29/00 604/544 |
| 2011/0238042 A1 | 9/2011 | Davis et al. |
| 2013/0152823 A1* | 6/2013 | Fouda .................... A01N 59/16 106/403 |
| 2013/0165905 A1* | 6/2013 | Pinchuk ............ A61M 25/0017 604/544 |
| 2013/0331824 A1* | 12/2013 | Kim .................. A61M 25/0026 604/544 |
| 2017/0014617 A1* | 1/2017 | Huici ..................... A61M 39/24 |
| 2017/0172778 A1* | 6/2017 | Brister ..................... A61F 5/003 |
| 2017/0173322 A1* | 6/2017 | Bonham ............... A61M 39/10 |
| 2017/0290598 A1* | 10/2017 | Culbert ............. A61M 25/0054 |
| 2018/0303655 A1 | 10/2018 | Glithero et al. |
| 2018/0344234 A1 | 12/2018 | McKinney et al. |

* cited by examiner

INDWELLING DOUBLE OR TRIPLE LUMEN URINARY CATHETER

FIELD OF THE INVENTION

The present invention generally relates to a double or triple lumen, indwelling urinary catheter having a bladder-protecting tip and a fitted check-valve.

BACKGROUND OF THE INVENTION

An indwelling, urinary catheter is a catheter designed to be inserted through a patient's urethra into their bladder and held in place with a balloon filled with sterile water. The general purpose of the catheter is to drain urine from the bladder. One of the most common kinds of indwelling catheters is a Foley catheter. The Foley catheter typically has two separate lumens or channels, one of which passes all the way through the catheter to allow urine to be collected into a collection bag. Sometimes other fluids (e.g., blood) or even solids (e.g., blood clots) need to pass from the bladder through a catheter, particularly if the patient has undergone surgery or suffered a trauma. Foley catheters are typically designed to channel more than just liquids from a catheterized bladder.

Indwelling, urinary catheters, specifically Foley catheters, suffer from several problems including bladder damage as well as the potential for infections. Bladder damage such as irritation or bladder lining trauma can be caused by poorly designed catheters. Little attention has been paid to this catheter design problem. Infections can result from bladder damage and from the fluid flow reversal in the catheter. The reverse flow can introduce bacteria into the bladder, which can in turn cause a painful bladder or urinary tract infection. While various approaches to one-way flow have been published (e.g., see U.S. Pat. Nos. 5,800,339 and 10,179,232 and US Patent Publication Nos. 2004/0172009, 2007/0161949, 2008/0051763, and 2011/0238042), these approaches can suffer from manufacturing difficulties and unusual designs that are difficult to adopt to everyday use.

Thus, there is an ongoing need for an indwelling, urinary catheter that protects the bladder, prevents reversal of urine flow, and is easily incorporated into current medical practices.

SUMMARY OF THE INVENTION

In an aspect, the present invention provides a novel indwelling, urinary catheter that is a double lumen catheter.

In another aspect, the present invention provides a novel indwelling, urinary catheter that is a triple lumen catheter.

These and other aspects, which will become apparent during the following detailed description, have been achieved by the inventors' discovery of a catheter that is protective of the bladder and prevents unwanted reversal of urine flow.

BRIEF DESCRIPTION OF THE DRAWINGS

FIG. 1A shows a double lumen, Foley catheter. FIG. 1B shows a triple lumen, Foley catheter having a bladder irrigation port. FIG. 1C shows a triple lumen, Foley catheter having a thermometer port.

FIG. 2A shows the top of the catheter tip with an optional irrigation port. FIG. 2B shows a cut-away side view of the catheter tip. FIGS. 2C-D show angular views of the angular catheter tip wherein the tip has an irrigation port in FIG. 2C, but not in FIG. 2D. FIG. 2E is a photograph of a side view of the catheter tip and the upper portion of an inflated balloon.

FIG. 3A shows a top, perspective view of the housing, including the notches. FIGS. 3B-C show cross-sectional views of the housing, including the notches. FIG. 3D shows a cross-sectional view of the housing and arrester bar.

DETAILED DESCRIPTION OF THE PREFERRED ASPECTS

Figure 1A:
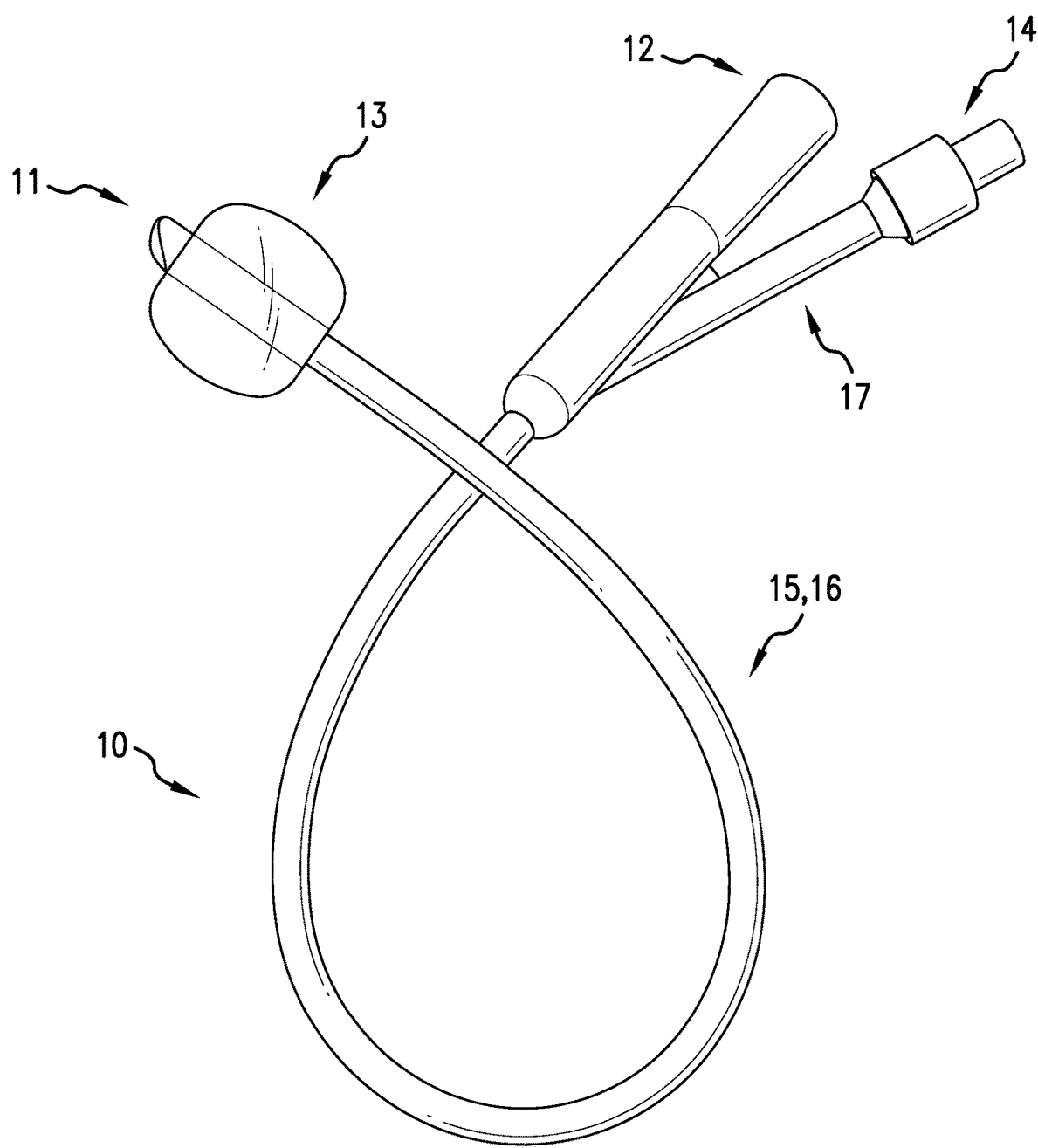
FIGS. 1A-C show three different catheter types in accordance with different aspects of the present invention.
Figure 1B:
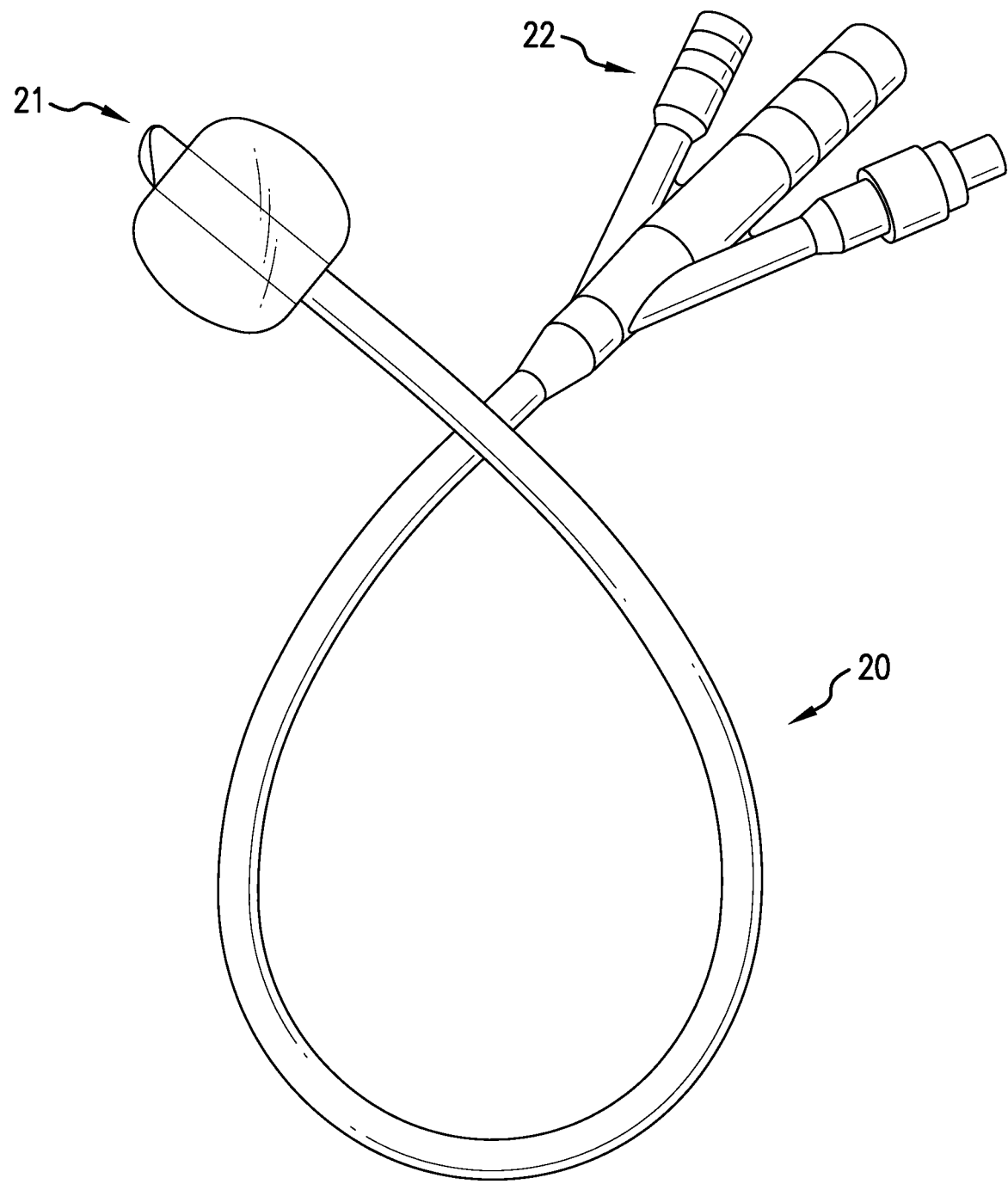

Exemplary aspects of the present invention are described with reference to the figures, where appropriate. Although the following detailed description contains many specifics for purposes of illustration, a person of ordinary skill in the art will appreciate that variations and alterations to the following details are within the scope of the invention. Accordingly, the following aspects of the invention are set forth without any loss of generality to, and without imposing limitations upon, the claimed invention.

An indwelling catheter is a catheter designed to be inserted through a patient's urethra into their bladder and held in place with a balloon filled with sterile water (or other appropriate fluid or gas). The purpose of the catheter is generally to drain urine from the bladder. One of the most common kinds of indwelling catheters is a Foley catheter. The Foley catheter typically has two separate lumens or channels, one of which passes all the way through the catheter to allow urine to be collected into a collection bag. Sometimes other fluids (e.g., blood) or even solids (e.g., blood clots) can pass from the bladder through a catheter, particularly if the patient has undergone surgery or suffered from some type of trauma. Thus, a catheter is typically designed to channel more than just liquids (urine) from a catheterized bladder.

The following table provides a description of the number structures in FIGS. 1-8.

| # | Structure |
| --- | --- |
| 10 | Double lumen, Foley catheter |
| 11 | Catheter tip |
| 12 | Funnel drainage port |
| 13 | Anchor balloon (balloon) |
| 14 | Balloon port |
| 15 | First lumen |
| 16 | Second lumen |
| 17 | Second end of the tubular catheter body |
| 20 | Triple lumen, Foley catheter |
| 21 | Catheter tip |
| 22 | Bladder irrigation port |
| 30 | Triple lumen, Foley catheter |
| 31 | Catheter tip |

-continued

| # | Structure |
|---|---|
| 32 | Thermometer port |
| 40 | Angular upper portion of the catheter tip |
| 41 | Irrigation port |
| 42 | Angular side of catheter tip |
| 43 | Anchor balloon (balloon) |
| 44 | Drainage port |
| 45 | Lower portion of the catheter tip |
| 50 | Check-valve |
| 51 | Opposing notches |
| 52 | Tapered housing |
| 53 | Proximal inlet |
| 54 | Distal outlet |
| 55 | Proximal outer ring |
| 56 | Proximal inner ring |
| 60 | Arrester bar |
| 70 | Valve sphere |
| 80 | Negative pressure air vent |
| 90 | Double lumen catheter |
| 91 | Fluid receptacle |
| 92 | Fluid bag |
| 93 | Flexible tubing |
| 94 | Receptacle nlet port |
| 95 | Receptacle Outlet port |
| 96 | Receptacle isual volume guide |
| 97 | Drainage bag outlet port |

Thus, in an aspect, the present invention provides a novel indwelling catheter, comprising:
a. a catheter tip (11), comprising:
  i. an angular upper portion (40), comprising: a drainage port (44) centered at the end of the catheter and extending through the lower portion; and,
  ii. a lower portion (45);
b. a tubular catheter body, comprising:
  i. a first end that is in contact with the lower portion of the tip;
  ii. a second end (17);
  iii. a first lumen (15) that connects the second body end to the drainage port;
  iv. an inflatable, anchor balloon (13) located near the first end of the body and near the lower portion of the catheter tip; and,
  v. a second lumen (16) that connects the balloon to the second body end;
c. a funnel drainage port (12) that is in liquid communication with the drainage port (44) via the first lumen, the port, further comprising:
  i. a check-valve (50), fitted into the funnel drainage port, the valve comprising:
    1. a tapered housing (52), comprising:
      a. a proximal inlet (53);
      b. a distal outlet (54) that is wider than the inlet; and,
      c. opposing notches (51) located on the inside of the housing near the outlet;
    2. a valve sphere (70) having a diameter slightly larger than the inlet; and,
    3. an arrester bar (60) that is in contact with the opposing notches of the housing; and,
d. a balloon port (14) that is in liquid communication with the balloon of the tubular body via the second lumen of the tubular body and is configured to receive liquid to inflate the balloon.

Proximal, proximal end, and proximal opening each refer to the end of the catheter that would reside in (or towards) the center of the body (or the bladder). The distal end of the catheter would be the opening that is furthest away from the center of the body (or the bladder).

With references to FIGS. 1A-1C and 2E, the catheter tip (e.g., 11, 21, and 42) on the indwelling catheter is the part of the catheter that extends from the edge of the inflated balloon to the proximal (bladder) end of the catheter. The catheter tip of the present invention is designed to reduce bladder trauma that can be caused by standard tips that typically have 1-2 side (bilateral or staggered) drainage ports (which would drain perpendicular to the present catheter tip, see FIGS. 2A (44) and 2E).

A typical catheter tip is around 15 mm as measured from the end of the tip to the inflated balloon. In another aspect, the length of the present catheter tip is from 4, 5, 6, 7, to 8 mm. In another example, the length is from 5 to 6 mm. This reduced size allows for a smaller presence in the bladder, thereby reducing a common cause of bladder trauma (i.e., the bladder collapsing onto a catheter tip causing potential irritation and/or trauma to the bladder).

Figure 2A:
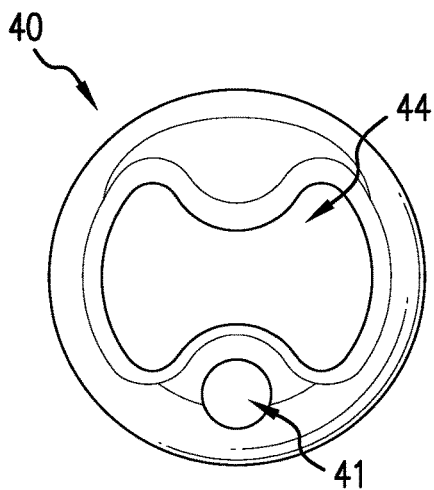
FIGS. 2A-E show top, side, and perspective views of the catheter tip.
Figure 2B:
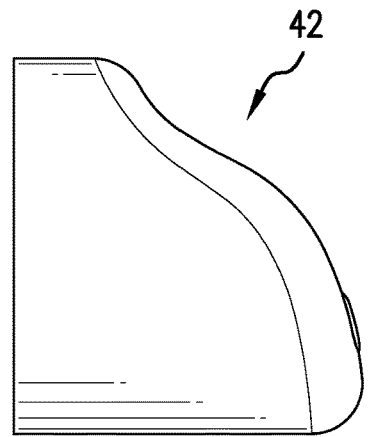
Figure 2C:
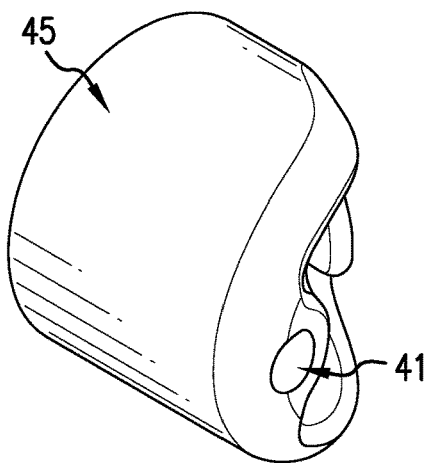
Figure 2D:
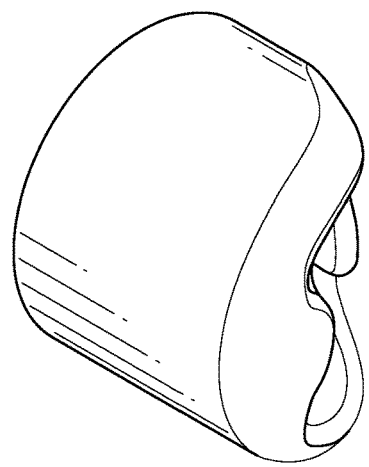
Figure 2E:
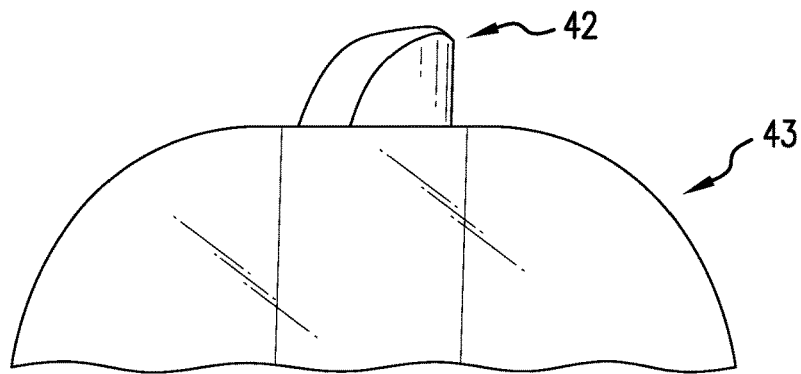
Figure 3A:
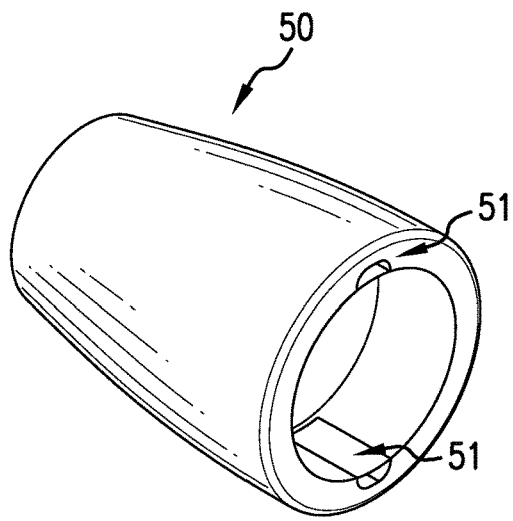
FIGS. 3A-D show different views of the check-valve housing.
Figure 3B:
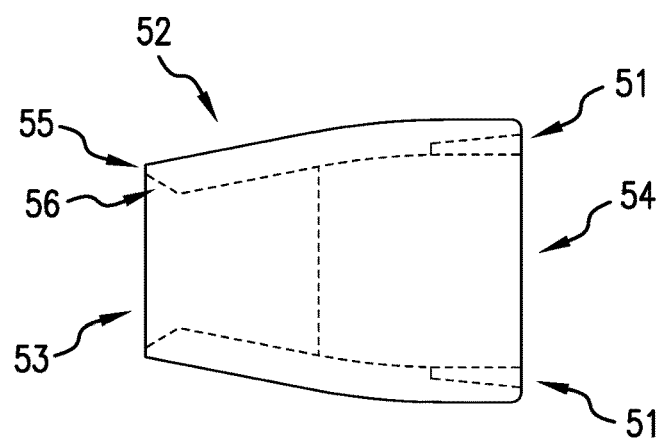
Figure 3C:
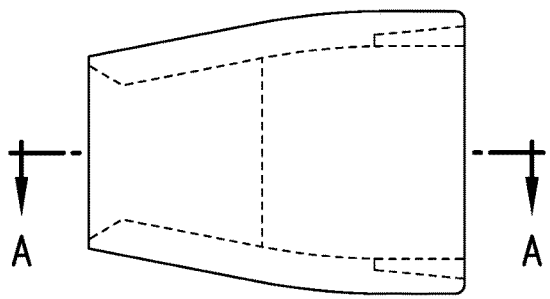
Figure 3D:
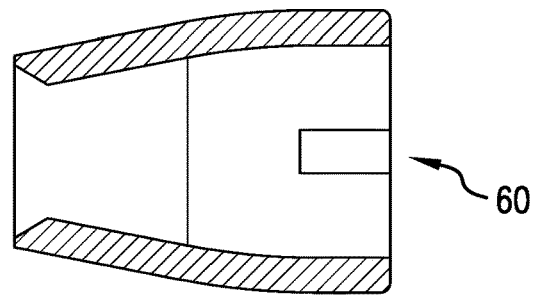
Figure 4A:
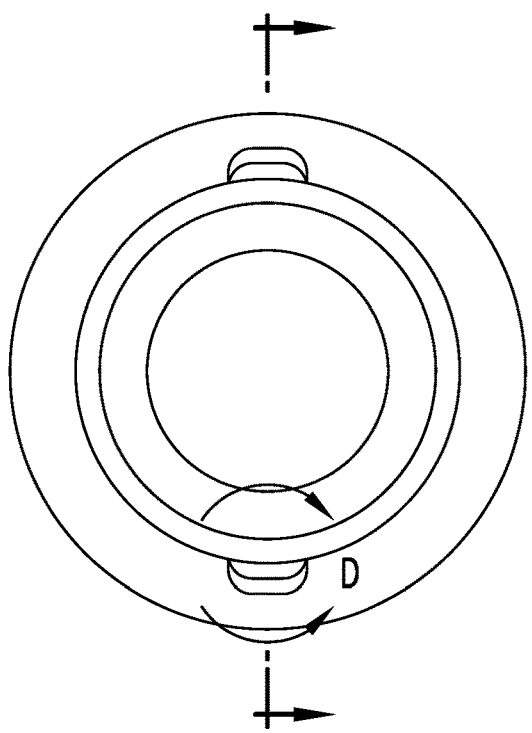
FIGS. 4A and 4B show a top view of the housing and an expanded view (View D) of a notch in the housing, respectively.
Figure 4B:
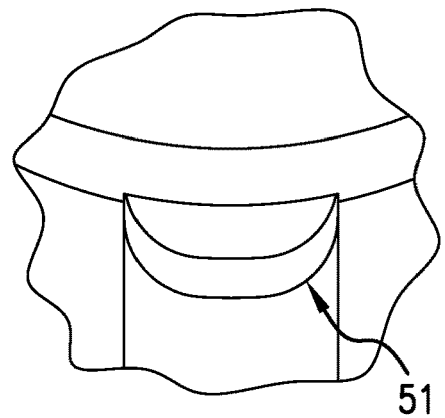

With reference to FIGS. 2A-E, the drainage port (44) of the catheter tip is centered at the end of the catheter (see FIG. 2A) and extends through the lower portion and one half of the upper portion angles downward from than opposing, second half, thereby forming an angular end on the catheter tip (see FIGS. 2B-D). This results in a tip that is hemispherical (has the shape of a half-circle) at the tip and gradually becomes round at the bottom of the angle (where the opening becomes enclosed by the remainder of the tip. FIGS. 2A and 2C also shows an optional irrigation port (44) adjacent to the drainage port. FIG. 2D shows the angular view of the tip without the optional irrigation port.

The funnel drainage port (see FIGS. 1A-C) (12 in FIG. 1A) is in liquid communication with the drainage port of the catheter tip via the first lumen (15) of the tubular body and is configured to allow bladder liquid to flow through it.

In another aspect, the funnel drainage port (12) is configured to be attached to tubing (flexible or rigid) either directly or through a tubing connector.

The check-valve (50) is fitted into the funnel drainage port (12). For example, the check-valve can be inserted (e.g., pushed or pressed from the distal end) into the funnel drainage port until it (the housing thereof or at least a portion of the housing) forms a liquid seal with the funnel. In another aspect, the tapered housing (52) mirrors the shape (e.g., conical) of the funnel drainage port (see FIGS. 3A-D).

With reference to FIGS. 3A-D and 6A-B, in the check-valve (50), the proximal inlet (53) is configured to allow bladder drainage to enter and the distal outlet (54) is configured to allow bladder drainage to exit. This is achieved by the outlet being wider (larger diameter) than the inlet. As see in FIGS. 3A-C, the opposing notches (51) located on the inside of the housing near the outlet (54) typically are at the end of the housing and provide openings for the arrester bar to slide into (e.g. snap into) the housing.

Figure 6A:
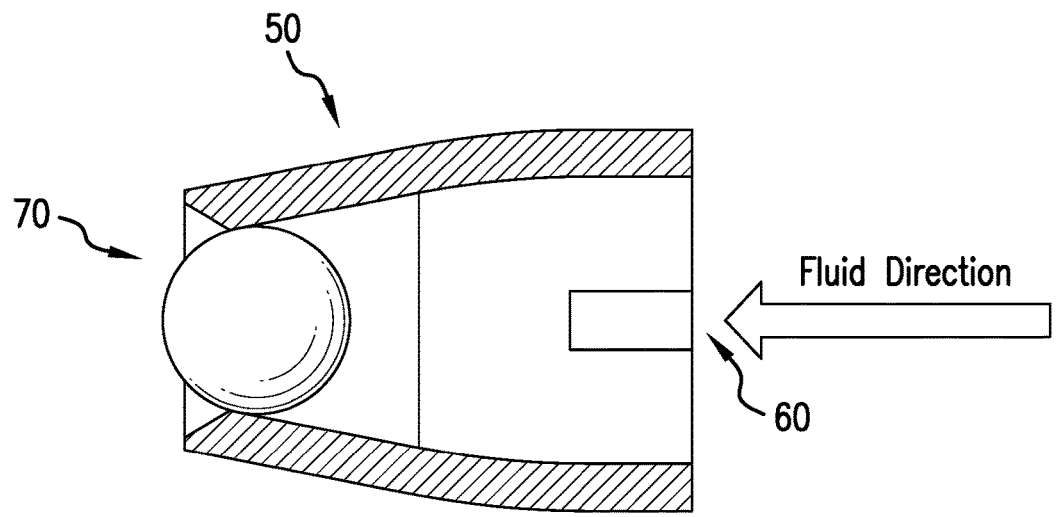
FIGS. 6A-6B show side views of the check-valve closed (6A) and open (6B).
Figure 6B:
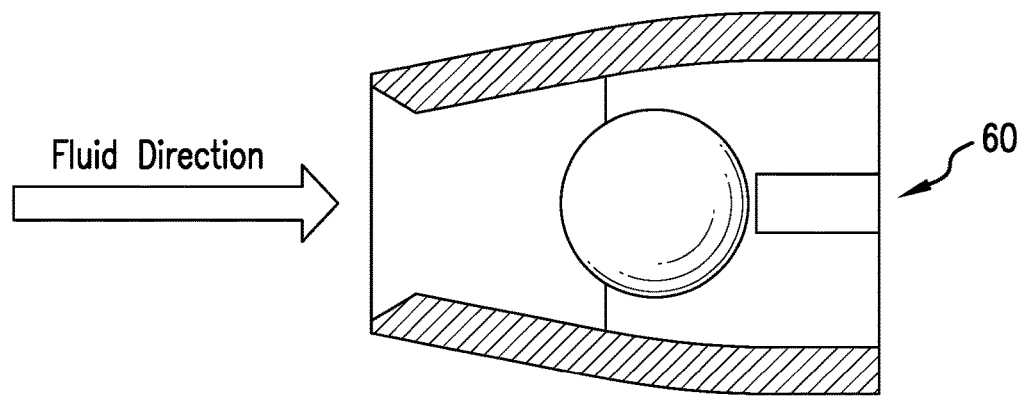

The valve sphere (70) diameter, which is slightly larger than the inlet, is such that the sphere can form a liquid seal with the inlet to prevent proximal flow of liquid (i.e., towards the catheter tip)(see FIGS. 6A-B).

Figure 5:
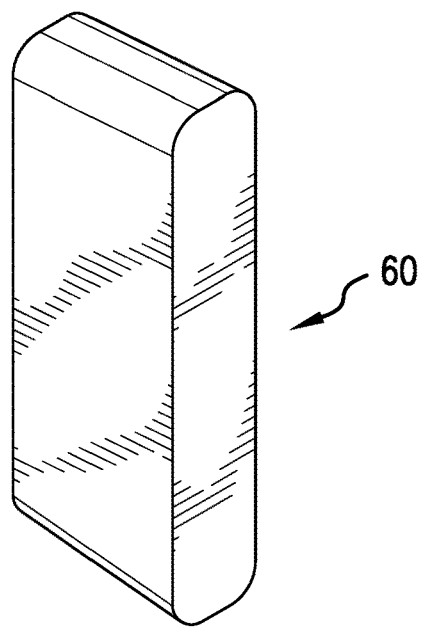
FIG. 5 show a perspective view of the arrester bar.

With reference to FIG. 5, the arrester bar (60), comprises: a top, bottom, two sides, and two ends. The bar is configured to span the opposing notches (51) of the housing (see FIGS. 4A-B), thereby allowing the ends of the bar to be in contact with the housing (50). The bar keeps the sphere inside the housing when fluid drains through the catheter (see FIG. 6B). In another aspect, the distance between the valve sphere and bottom of the arrester bar, when the valve sphere is in contact with the inlet (i.e., the check valve is sealed)(see FIG. 6A), is about the diameter of the sphere. In another aspect, the width of the outlet minus the width of the bar is greater than the width of the inlet.

With reference to FIGS. 3B-D and 6A-B, the proximal opening of the check valve housing can have an inward taper, which results in the proximal opening having an inner ring (56) and an outer ring (55). The inner ring is located on the inward taper and is smaller in diameter than the valve sphere (thereby allowing the sphere to seal with the inner ring)(see FIG. 6A). In another aspect, the outlet's diameter (see FIG. 3D) is more than 50% larger than the inlet's diameter (for housings with or without an inward taper). In another example, the outlet's diameter is between 50, 51, 52, 53, 54, 55, 56, 57, 58, 59, to 60% larger than the inlet's diameter. In another aspect, the outlet diameter almost 50% larger that the diameter of the valve sphere.

A benefit of the check-valve component dimensions and shapes described herein is that the housing is large to allow enough room for liquid (e.g., urine) and potential particles (e.g., blood clots) to flow/move around the valve sphere, but small enough and shaped such that the valve sphere can rapidly close the valve if fluid begins to flow proximally.

As an example, the check valve has at least two of the following dimensions.
  a. housing height: 12.7 mm (0.5");
  b. proximal inner ring diameter: 4.57 mm (0.18");
  c. proximal outer ring diameter: 6.25 mm (0.25");
  d. distal end inner diameter: 7.11 mm (0.28");
  e. distal end outer diameter: 9.4 mm (0.37");
  f. valve sphere diameter: 4.8 mm (0.189");
  g. arrester bar height: 3.05 mm (0.12");
  h. arrester bar width: 1.52 mm (0.06");
  i. arrester bar length at top (distal side): 8.13 mm (0.32");
  j. arrester bar length at bottom (proximal side): 7.62 mm (0.30"); and,
  k. thickness of the tapered housing: 1.2 mm (0.04").

In another example, the check-valve has at least four of the above dimensions. In another example, the check-valve has all the above dimensions.

In another aspect, the valve sphere, comprises: rubber. The hardness of the valve sphere can be important for the sphere to have enough friction to form a good seal with the housing. A durometer is typically used to test the hardness of plastics and rubbers, with the Shore A Hardness scale being used to measure the hardness of flexible rubbers. The Shore A scale ranges from 0 (extra soft/soft) to 100 (hard/extra hard), with medium soft being about 40-60. In an aspect, the valve sphere has a Shore A hardness of from 40, 41, 42, 43, 44, 45, 46, 47, 48, 49, 50, 51, 52, 53, 54, 55, 56, 57, 58, 59, to 60. In another example, the hardness is from 50, 55, to 60.

In another aspect, the rubber is an acrylonitrile butadiene rubber. In another aspect, the rubber is Buna nitrile (Buna-N) rubber. In another aspect the rubber is Buna nitrile rubber with a Shore A hardness of from 50, 55, to 60. In another aspect, the Buna nitrile rubber has a hardness of 55.

In another aspect, the housing and arrester bar, comprise: a thermoplastic. It can be beneficial to autoclave the check valve to reduce the possibility of infection. Thus, in another aspect, the thermoplastic is configured to withstand standard autoclave temperatures (e.g., 121° C., 15 psi, for about 30 minutes). Examples of thermoplastic include polyethylene and polypropylene. In another aspect, the housing and arrester bar are clear or translucent. In another aspect, the arrester bar is secured to the housing by friction between the bar and the housing. In another aspect, the arrester bar is configured to snap into the opposing notches in the housing and remain secured by friction between the bar and the housing. Typically, the housing and arrester bar are injection molded. Other methods of manufacturing can be used, such as 3D printing.

Alternatively, the housing and arrester bar are one continuous piece, but flexible enough to allow the valve sphere to be forced passed the bar and into the house to complete the construction of the check-valve. In this aspect, the ends of the arrester bar and the opposing notches into which the ends would fit are absent.

Alternatively, the housing and arrester bar are one continuous piece, except that one end of the bar is not formed into the housing, but rather can be snapped into it (similar to both ends when the housing and arrester bar are two separate pieces). This would allow for the ball to be more easily pressed into the housing (compared to a fully continuous unit). In this aspect, one end of the arrester bar and the corresponding notch into which this end would fit are absent.

In another aspect, the housing, further comprises: at least one protrusion on the outside thereof. For example, the protrusion(s) can be a ridge that is continuous (circumscribes the house) to form a ring or a non-continuous (does not fully circumscribe the housing) or a plurality of continuous or non-continuous protrusions. The protrusion(s) can aid in securing the housing to the inside of the funnel drainage port.

In another aspect, the present invention provides a novel check-valve as described herein.

In another aspect, the inflatable, anchor balloon located near the first end of the body is also located near the lower portion of the catheter tip. The inflatable, anchor balloon is in liquid contact with the second lumen, and is a sufficient size, upon inflation, to anchor the catheter in the bladder.

Typically, the tubular catheter body houses both the first and second lumens. In another aspect, the balloon and second lumen surround the first lumen (but are not in liquid contact therewith).

In another aspect, the balloon is capable of being inflated to a final volume selected from 5, 10, 15, 20, 25, 30, 35, 40, 45, 50, 55, 60, 65, 70, to 75 cc. In another example, the balloon volume is selected from: 5, 10, and 30 cc.

The thickness of a catheter is defined as its French gauge. Examples of the thickness of the catheters of the present invention include 1, 2, 3, 4, 5, 6, 7, 8, 9, 10, 11, 12, 13, 14, 15, 16, 17, 18, 19, 20, 21, 22, 22, 24, 26, 28, 30, 32, and 34. Additional examples include 16 and 18.

In another aspect, the catheter, further comprises:
  e. a negative pressure air vent (80) that is in air communication with the funnel drainage port.

Figure 7:
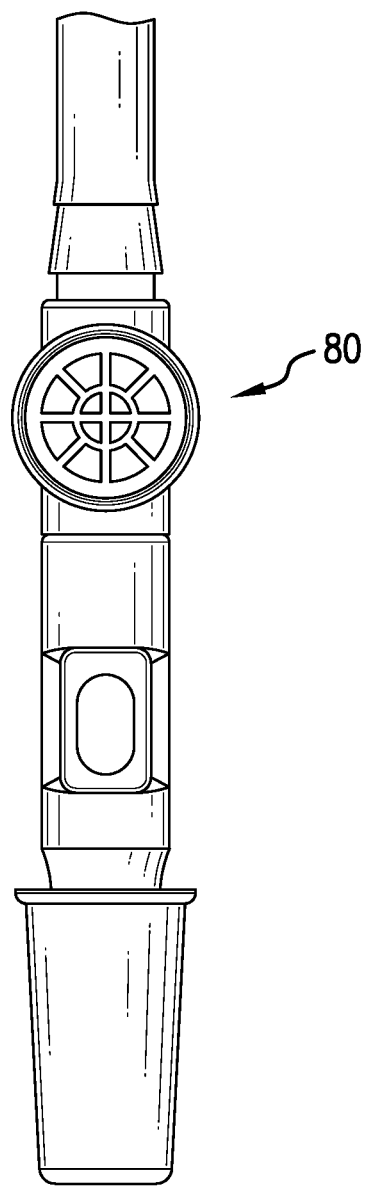
FIG. 7 shows a top view of an air vent.

With reference to FIG. 7, the negative pressure air vent is typically located distal to the check-valve. In another aspect, the air vent, comprises: a filter that prevents liquid (or solids) from exiting the vent, but allows air to enter the vent (and thereby the catheter). The benefit of the negative pressure is that it reduces (or eliminates) negative air pressure in the system. This in turn reduces a potential vacuum effect inside the bladder, which allows the bladder to softly collapse onto the catheter tip (as opposed to a potentially rapid or forced collapse caused by negative pressure). In another aspect, the negative pressure air vent is connected to the funnel drainage port via tubing (see FIG. 7). For example, the tubing can be flexible (e.g., same material as the catheter or another material such as polyvinyl chloride (PVC)) or stiff (e.g., a harder plastic such as a harder PVC). Alternatively, the negative pressure air vent is located on the funnel of the funnel drainage port (not shown).

In another aspect, the catheter, further comprises:
f. a bladder irrigation port (22);
wherein:
  a. the catheter tip, further comprises:
    iii. an irrigation port (41) in the upper portion, the irrigation port being adjacent to one side of the drainage port (44) and extending through the lower portion of the tip;
  b. the tubular catheter body, further comprises:
    vi. a third lumen that connects the irrigation port to the bladder irrigation port.

In this aspect, the catheter is a triple lumen catheter (e.g., a Foley triple lumen catheter) and the bladder irrigation port is in liquid communication with the irrigation port via the third lumen and is configured to receive irrigation liquid (e.g., saline) and optionally medications (e.g., an antibiotic) to be introduced into the bladder. With reference to FIGS. 2A and 2C, the irrigation port (41) is located at the end of the catheter tip and is adjacent to the drainage port (44) of the catheter tip (also see FIG. 1B). The irrigation port is typically located on the longer end of the catheter tip. Alternatively, the irrigation port is located on the shorter end of the catheter tip (at the bottom of the angle)(not shown). For catheters where irrigation is not required, the irrigation port is absent from the catheter tip (see FIG. 2D).

In another aspect, the catheter, further comprises:
g. a thermometer port (32);
wherein:
  a. the catheter tip, further comprises:
    iii. a temperature sensor enclosed in the catheter tip;
  b. the tubular catheter body, further comprises:
    vi. a third lumen that connects the temperature sensor to the thermometer port.

Figure 1C:
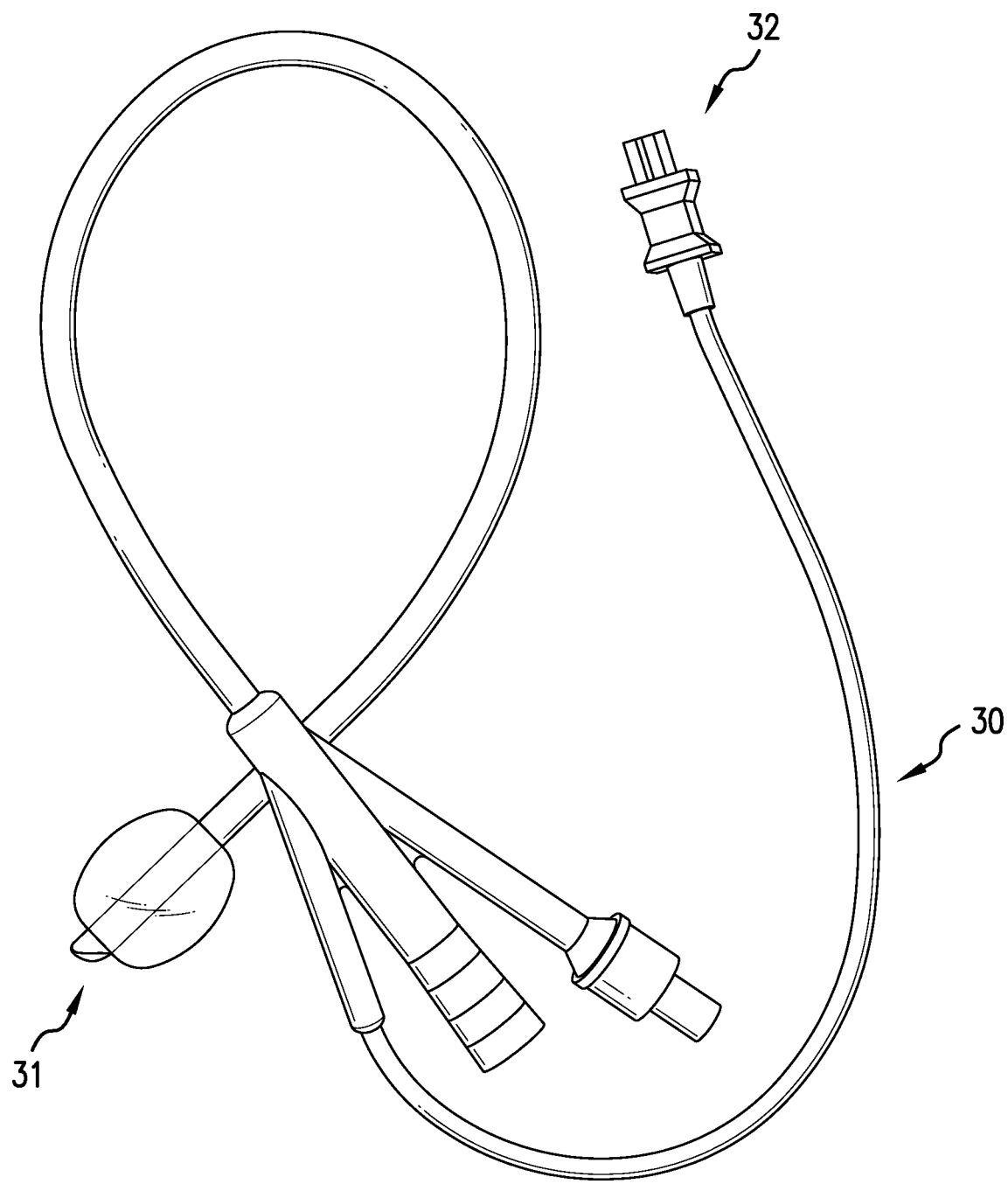

In this aspect, the catheter is a triple lumen catheter (e.g., a Foley triple lumen catheter) and the thermometer port is in electronic (e.g., wire(s)) or thermal communication (e.g., a liquid or solid that transfers heat) with the temperature sensor via the third lumen (see FIG. 1C). The temperature sensor is enclosed in the catheter tip and is configured to sense the temperature of the bladder (or fluid therein) through the catheter tip (e.g., through the elastomeric material forms the catheter tip). If the temperature sensor is longer than the tip itself, then part of the sensor will extend into the third lumen of the tubular body. As an example, the thermometer port is a 2-port connector that is configured to connect with a display (e.g., a digital display).

In another aspect, the catheter tip, body, funnel drainage port, and balloon port (and optionally third lumen—for bladder irrigation or thermometer) are comprised of an elastomeric material selected from silicone and latex. It can be beneficial to coat the catheter, particularly when it is latex, to avoid an allergic reaction (e.g., a latex allergy) or to provide lubrication to simplify catherization. The coating is typically present on the tip and body as it is generally unnecessary to coat the distal end of the catheter. Examples of the coating (lubricating agent) include silicon, hydrogel, polytetrafluoroethylene, and combinations thereof.

In another aspect, the catheter material, further comprises: a bactericidal agent (an agent that kills bacteria). In this aspect, the bactericidal agent is coated on the catheter material (e.g., dipping or spraying onto the catheter).

In another aspect, the coating, further comprises: a bactericidal agent. In this aspect, the agent is typically mixed with the coating prior to applying it to the catheter.

In another aspect, the bactericidal agent is selected from: chlorhexidine, a silver agent (e.g., silver sulfadiazine, silver phosphate, and silver nanoparticles), and a combination thereof.

In another aspect, the catheter, further comprises:
h. a fluid receptacle (91) in liquid communication with the funnel drainage port, the receptacle comprising:
  i. an inlet port (94) proximal to the catheter tip;
  ii. an outlet port (95) distal to the catheter tip; and,
  iii. a visual volume guide (96) to determine the volume of liquid collected.

Figure 8:
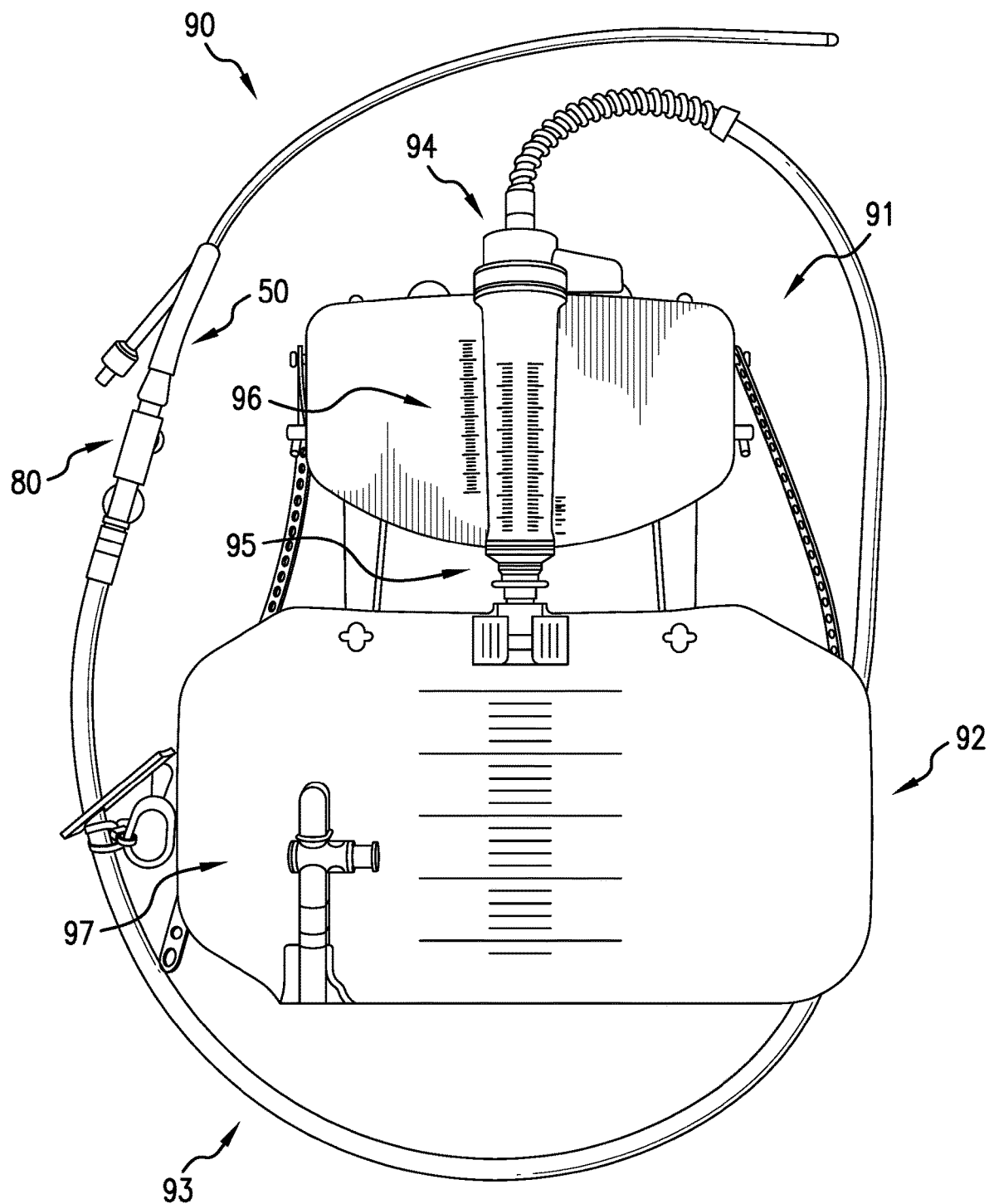
FIG. 8 shows a photograph of the front of a double lumen catheter, with an air filter, connected via flexible tubing to a fluid receptacle, which is connected to a fluid bag.

The fluid receptable (91) can be flexible (e.g., a soft plastic or silicone bag) or rigid (e.g., a rigid plastic such as PVC). In another aspect, the fluid receptable is connected to the funnel drainage port via flexible tubing (93)(e.g., silicone, latex, or PVC). With reference to FIG. 8, the fluid receptacle (91) is connected to the negative air pressure vent (80) via flexible tubing (93); and the vent is connected to the funnel drainage port as described above. Alternatively, when the vent is a part of the funnel drainage port (or the vent is absent), the fluid receptacle is directly connected to the funnel drainage port via flexible tubing.

In another aspect, the flexible tubing is PVC. In another aspect, the flexible tubing, further comprises: a bacteriostatic agent (e.g., an agent that-stops or substantially reduces bacteria from reproducing). An example of a bacteriostatic agent is zinc oxide (e.g., zinc oxide nanoparticles).

In another aspect, the fluid receptacle, further comprises: a dating system on the front (the same side as the visual volume guide (96))(see FIG. 8). The dating system advantageously allows for the healthcare practitioner to write (or mark via ink or a sticker) the date of catheter insertion.

In another aspect, the fluid receptacle, further comprises: a means for hanging the receptacle (e.g., on a patient's bed). Examples of the hangar include a strap (e.g., a plastic strap with multiple attachment points (e.g., holes) to allow for a variety of strap lengths, a hook (e.g., plastic or metal), and a length of fabric (e.g., cloth or plastic) having a hook and loop attachment system.

In another aspect, the catheter, further comprises: a drainage bag (92), comprising an inlet port configured to attach to the outlet port of the fluid receptable (see FIG. 8). In another aspect, the drainage bag, further comprises: an outlet port (97) distal to its inlet port (see FIG. 8). The drainage bag can be removed from the catheter to discard collected fluid. Alternatively, the drainage bag can be drained into another receptacle.

Numerous modifications and variations of the present invention are possible considering the above teachings. It is therefore to be understood that within the scope of the appended claims, the invention may be practiced otherwise that as specifically described herein.

I claim:
1. An indwelling, urinary catheter, comprising:
  a) a urinary catheter tip, comprising:
    i) an elongated portion, comprising: parallel sides, a tip end, and a boundary with a lower portion and, further comprising:
      A a profile with a non-linear slope from the tip end to the boundary, wherein the slope near the tip end is concave and the slope near the boundary is convex;
      B a drainage port comprising: a circumference and a concave indentation that disrupts the continuity of the circumference thereof, the drainage port being centered at the end of the catheter tip, extending through the lower portion, and running parallel to a second lumen; and,
ii) the lower portion, comprising parallel sides, wherein the sides of the lower portion are parallel to the sides of the elongated portion;
b) a tubular urinary catheter body, comprising:
i) a first body end that is in contact with the lower portion of the catheter tip and, comprising: sides that are parallel with one another and with the sides of the elongated and lower portions of the urinary catheter tip;
ii) a second body end;
iii) a first lumen that connects the second body end to the drainage port;
iv) an inflatable, anchor balloon located near and circumscribing the first body end of the tubular catheter body; and,
v) the second lumen that connects the balloon to the second body end;
c) a funnel drainage port that is in liquid communication with the drainage port via the first lumen, the funnel drainage port, further comprising:
i) a check-valve, fitted into the funnel drainage port, the valve comprising:
C a tapered housing having an inside and an outside, comprising:
a) a proximal inlet having a diameter;
b) a distal outlet having a diameter that is wider than the diameter of the proximal inlet; and,
c) opposing notches located on the inside of the housing near the outlet;
D a valve sphere having a diameter larger than the inlet; and,
E an arrester bar that is in contact with the opposing notches of the housing; and,
d) a balloon port that is in liquid communication with the balloon of the tubular catheter body via the second lumen of the tubular body and is configured to receive liquid to inflate the balloon;
wherein:
the balloon is capable of being inflated to a final volume of from 5-75 cc;
the length of the catheter tip is from 4-8 mm as measured from the end of the tip to the balloon, when inflated; and,
the catheter is configured to be an indwelling, urinary catheter.

2. The urinary catheter of claim 1, wherein the urinary catheter, further comprises:
e) a negative pressure air vent that is in air communication with the funnel drainage port.

3. The urinary catheter of claim 2, wherein the negative pressure air vent is present in tubing connected to the funnel drainage port.

4. The urinary catheter of claim 3, wherein the urinary catheter, further comprises:
i) a fluid receptacle in liquid communication with the funnel drainage port, the receptacle comprising:
i) an inlet port proximal to the catheter tip;
ii) an outlet port distal to the catheter tip; and,
iii) a visual volume guide to determine the volume of liquid collected; and,
j) flexible tubing connecting the fluid receptacle to the tubing comprising the negative air pressure tubing.

5. The urinary catheter of claim 4, wherein the flexible tubing, further comprises: zinc oxide nanoparticles.

6. The urinary catheter of claim 1, wherein the urinary catheter is a Foley catheter.

7. The urinary catheter of claim 1, wherein the urinary catheter, further comprises:
f) A bladder irrigation port;
wherein:
a) the urinary catheter tip, further comprises:
iii) an irrigation port in the elongated portion, the irrigation port being adjacent to the concave indentation in the drainage port and extending through the lower portion of the tip;
b) the urinary tubular catheter body, further comprises:
vi) a third lumen that connects the irrigation port to the bladder irrigation port.

8. The urinary catheter of claim 1, wherein the urinary catheter, further comprises:
g) a thermometer port;
wherein:
a) the urinary catheter tip, further comprises:
iii) a temperature sensor enclosed in the catheter tip and being adjacent to the concave indentation in the drainage port;
b) the urinary tubular catheter body, further comprises:
vi) a third lumen that connects the temperature sensor to the thermometer port.

9. The urinary catheter of claim 1, wherein the balloon is capable of being inflated to a final volume selected from: 5, 10, and 30 cc.

10. The urinary catheter of claim 1, wherein the proximal opening of the check valve housing has an inward taper, an inner ring, and an outer ring, wherein the inner ring is located on the inward taper and the inner ring is smaller in diameter than the valve sphere.

11. The urinary of claim 1, wherein the distal outlet diameter is 50% larger than a diameter of the valve sphere.

12. The urinary catheter of claim 1, wherein the distal outlet diameter is more than 50% larger than that of the diameter of the proximal inlet.

13. The urinary of claim 1, wherein the valve sphere, comprises: rubber.

14. The urinary catheter of claim 13, wherein the rubber is acrylonitrile butadiene rubber and has a Shore A hardness of from 50-60.

15. The urinary catheter of claim 13, wherein the rubber is Buna nitrile rubber.

16. The urinary catheter of claim 15, wherein the rubber has a Shore A hardness of 55.

17. The urinary catheter of claim 1, wherein the housing and arrester bar, comprise: a thermoplastic selected from: polyethylene and polypropylene.

18. The urinary catheter of claim 1, wherein the arrester bar is configured to snap into the opposing notches in the housing and remain secured by friction between the bar and the housing.

19. The urinary catheter of claim 1, wherein the urinary catheter tip, body, funnel drainage port, and balloon port are comprised of a urinary catheter material selected from silicone and latex.

20. The urinary catheter of claim 1, wherein the urinary catheter, further comprises:
h) a fluid receptacle in liquid communication with the funnel drainage port, the receptacle comprising:
i) an inlet port proximal to the catheter tip;
ii) an outlet port distal to the catheter tip; and,
iii) a visual volume guide to determine the volume of liquid collected.

21. The urinary catheter of claim 20, wherein the urinary catheter, further comprises: flexible tubing connecting the fluid receptacle to the funnel drainage port.

22. The urinary catheter of claim 21, wherein the flexible tubing, further comprises: zinc oxide nanoparticles.

23. The urinary catheter of claim 1, wherein the thickness of the urinary catheter is 16 gauge.

24. The urinary catheter of claim 1, wherein the thickness of the urinary catheter is 18 gauge.

* * * * *